US00PP22863P2

(12) United States Plant Patent

Klemm et al.

(10) Patent No.: US PP22,863 P2

(45) Date of Patent: Jul. 17, 2012

(54) *BIDENS* PLANT NAMED 'KLEBF10709'

(50) Latin Name: *Bidens ferulifolia*
Varietal Denomination: KLEBF10709

(75) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 13/065,804

(22) Filed: Mar. 29, 2011

(51) Int. Cl.
*A01H 5/00* (2006.01)

(52) U.S. Cl. ..... Plt./410

(58) Field of Classification Search ..... Plt./410
See application file for complete search history.

*Primary Examiner* — Annette Para

(74) *Attorney, Agent, or Firm* — Jondle & Associates, P.C.

(57) ABSTRACT

A new variety of *Bidens* plant named 'KLEBF10709' particularly characterized by strong vigor, early flowering, and bi-colored flowers, is disclosed.

1 Drawing Sheet

Genus and species: *Bidens ferulifolia.*
Variety denomination: 'KLEBF10709'.

BACKGROUND OF THE NEW PLANT

The present invention comprises a new and distinct variety of *Bidens*, botanically known as *Bidens ferulifolia*, and hereinafter referred to by the variety name 'KLEBF10709'. 'KLEBF10709' was discovered in July 2007 in Stuttgart, Germany and originated from an open pollination between the proprietary female parent '07 0032' and an unknown male parent. A single plant selection was subsequently chosen for further evaluation and asexual propagation.

The new variety was first propagated via vegetative cuttings and in-vitro propagation in May 2008 in Stuttgart, Germany and has been asexually reproduced repeatedly by vegetative cuttings in Stuttgart, Germany for over six generations. 'KLEBF10709' has been found to retain its distinctive characteristics through successive asexual propagations.

Plant Breeder's Rights for this variety were applied for in Canada on Mar. 19, 2010. 'KLEBF10709' has not been made publicly available more than one year prior to filing of this application.

SUMMARY OF THE INVENTION

The following are the most outstanding and distinguishing characteristics of this new variety when grown under normal horticultural practices in a glass greenhouse in Stuttgart, Germany.

1. Strong vigor;
2. Early flowering; and
3. Bi-colored flowers.

DESCRIPTION OF THE PHOTOGRAPH

This new *Bidens* plant is illustrated by the accompanying photograph which shows a close-up of a flower of the plant. The colors shown are as true as can be reasonably obtained by conventional photographic procedures.

The photograph was taken on a plant about 3 months old grown from rooted cuttings in a 10 centimeter pot in a glass greenhouse in Stuttgart, Germany under normal horticultural practices.

DESCRIPTION OF THE NEW VARIETY

The following detailed descriptions set forth the distinctive characteristics of 'KLEBF10709'. The data which define these characteristics were collected from asexual reproductions carried out in Stuttgart, Germany. The plant history was taken in the Spring of 2010 on 3-month old plants grown in 10 centimeter pots in a glass greenhouse with a minimum pinch date of 8 weeks. The color readings were determined under natural light. Color references are to The R.H.S. Colour Chart of The Royal Horticultural Society of London (R.H.S.), Fifth Edition (2007).

DESCRIPTION OF THE NEW PLANT

Classification:
- *Family.*—Asteraceae.
- *Genus and species.*—*Bidens ferulifolia.*
- *Common name.*—*Bidens,* Beggarticks, Bur-marigold, tickseed.

Parentage:
- *Female parent.*—The proprietary female *Bidens* plant '07 0032'.
- *Male parent.*—Unknown.

Plant:
- *Propagation.*—Vegetative cuttings.
- *Time to initiate and develop roots.*—3 weeks.
- *Root description.*—Fine white roots with high density.
- *Rooting habit.*—Freely branching.
- *Appearance and type.*—Round to flat.
- *Habit.*—Upright to half hanging.
- *Height (from top of soil).*—12.0 cm to 15.0 cm.
- *Diameter (plant spread).*—8.0 cm to 10.0 cm.

Branches:
- *Color.*—Green.

Leaves:
- *Arrangement.*—Composed.
- *Shape.*—Ovate.

*Apex*.—Obtuse.
*Margin*.—Pinnate.
*Base*.—Acute.
*Color*.—Mature leaf: Upper surface: RHS 135A. Lower surface: RHS 137D.
*Venation*.—Pattern: Pinnate.
*Petioles*.—Length: 1.5 cm to 2.0 cm. Diameter: Less than 0.1 cm. Texture: Smooth. Color (both upper and lower surfaces): RHS 137D.

Inflorescence:
*Appearance*.—Daisy-type.
*Size*.—Diameter: 4.5 cm. Depth: 0.5 cm.
*Diameter of disc*.—0.5 cm.
*Number of inflorescences and buds per plant*.—15 to 25.
*Lastingness of individual blooms on the plant*.—3 to 4 days.
*Fragrance*.—Present.

Bud:
*Length*.—0.8 cm.
*Diameter*.—0.5 cm.
*Shape*.—Ovate.
*Color*.—Light brown-green.

Ray florets:
*Length*.—2.0 cm to 2.5 cm.
*Width*.—1.0 cm to 1.2 cm.
*Shape*.—Elliptical.
*Apex*.—Obtuse.
*Margin*.—Entire.
*Texture* (*both surfaces*).—Smooth.
*Number of ray florets per inflorescence*.—8.
*Color* (*when opening*).—Upper surface: RHS 21B.
*Color* (*when fully opened*).—Upper surface: RHS 8D margins with RHS 6A centers.

COMPARISON WITH PARENTAL AND COMMERCIAL VARIETIES

'KLEBF10709' differs from the female parent, the proprietary *Bidens* plant '07 0032', in that 'KLEBF10709' has a strong vigor and vibrant colored flowers, while '07 0032' has less vigor and weaker colored flowers.

'KLEBF10709' differs from the commercial cultivar, 'Fisbimex' (U.S. Plant Pat. No. 19,164), in that 'KLEBF10709' has leaves that are ovate shaped in a composed arrangement, while 'Fisbimex' has leave that are roughly deltoid, pinnatisect shaped with an opposite, decussate arrangement. In addition, the upper surface of the inflorescences of 'KLEBF10709' are yellow-orange colored when opening (RHS 21B) and then bi-colored pale yellow (RHS 8D) with darker yellow centers (RHS 6A), while the upper surface of the inflorescences of 'Fisbimex' are yellow-colored when opening (RHS 12B) and then solid yellow (RHS 12A).

We claim:

1. A new and distinct variety of *Bidens* plant named 'KLEBF10709' as shown and described herein.

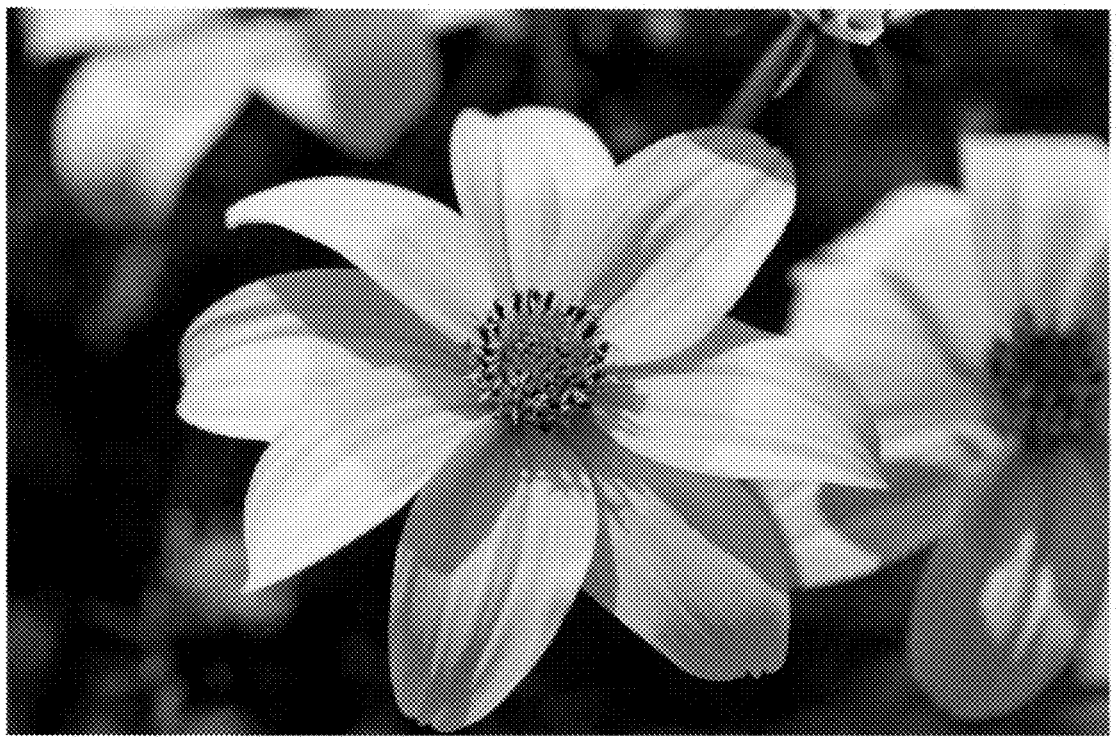

* * * * *